(12) United States Patent
Kobayashi

(10) Patent No.: US 7,729,469 B2
(45) Date of Patent: Jun. 1, 2010

(54) X-RAY IMAGING APPARATUS

(75) Inventor: Masaaki Kobayashi, Shimotsuke (JP)

(73) Assignee: Canon Kabushiki Kaisha, Tokyo (JP)

( * ) Notice: Subject to any disclaimer, the term of this patent is extended or adjusted under 35 U.S.C. 154(b) by 108 days.

(21) Appl. No.: 12/119,215

(22) Filed: May 12, 2008

(65) Prior Publication Data

US 2009/0092223 A1    Apr. 9, 2009

(30) Foreign Application Priority Data

May 14, 2007   (JP)   ............................. 2007-127539

(51) Int. Cl.
*A61B 6/00*   (2006.01)
*G01N 23/00*  (2006.01)
*G21K 1/12*   (2006.01)
*H05G 1/60*   (2006.01)

(52) U.S. Cl. ............................. 378/10; 378/17; 378/20; 378/69; 378/195; 378/196

(58) Field of Classification Search ................... 378/10, 378/17, 20, 69, 195, 196
See application file for complete search history.

(56) References Cited

U.S. PATENT DOCUMENTS

| 5,317,617 | A | 5/1994 | Lange | |
|---|---|---|---|---|
| 6,148,058 | A * | 11/2000 | Dobbs | 378/19 |
| 6,470,068 | B2 * | 10/2002 | Cheng | 378/20 |
| 7,058,158 | B2 * | 6/2006 | Sako | 378/17 |
| 2002/0080921 | A1 * | 6/2002 | Smith et al. | 378/189 |
| 2002/0181649 | A1 | 12/2002 | Rashe et al. | |

FOREIGN PATENT DOCUMENTS

| EP | 1364615 | 11/2003 |
|---|---|---|
| JP | 2005205082 A | 8/2005 |
| JP | 200643193 A | 2/2006 |
| WO | WO03/081220 | 10/2003 |

* cited by examiner

*Primary Examiner*—Hoon Song
*Assistant Examiner*—Mona M Sanei
(74) *Attorney, Agent, or Firm*—Canon U.S.A., Inc. I.P. Division

(57) ABSTRACT

An X-ray imaging apparatus includes an X-ray imaging unit, rotating unit configured to rotate a subject about an axis of rotation relative to the X-ray imaging unit, supporting unit configured to support the subject, and a limiting unit configured to limit the range in which the X-ray imaging unit is moveable along the axis of rotation depending on the position of the supporting means relative to the axis of rotation.

4 Claims, 5 Drawing Sheets

Legend:
11 = X-ray tube
12 = rotating table
13 = X-ray imaging unit
14 = slide unit; 15 = column
16 = up-and-down drawing unit
17 = image taking unit
18 = rotary drive unit
19 = chair; 20 = backrest
21 = lower limb guard
22 = belt; 23 = handle
24 = chair slide member
25 = backrest slide member
26 = chair position detector
27 = backrest position detector
31 = control unit
32 = X-ray generation apparatus
33 = image taking unit
34 = footswitch
35 = image processing unit

FIG. 1

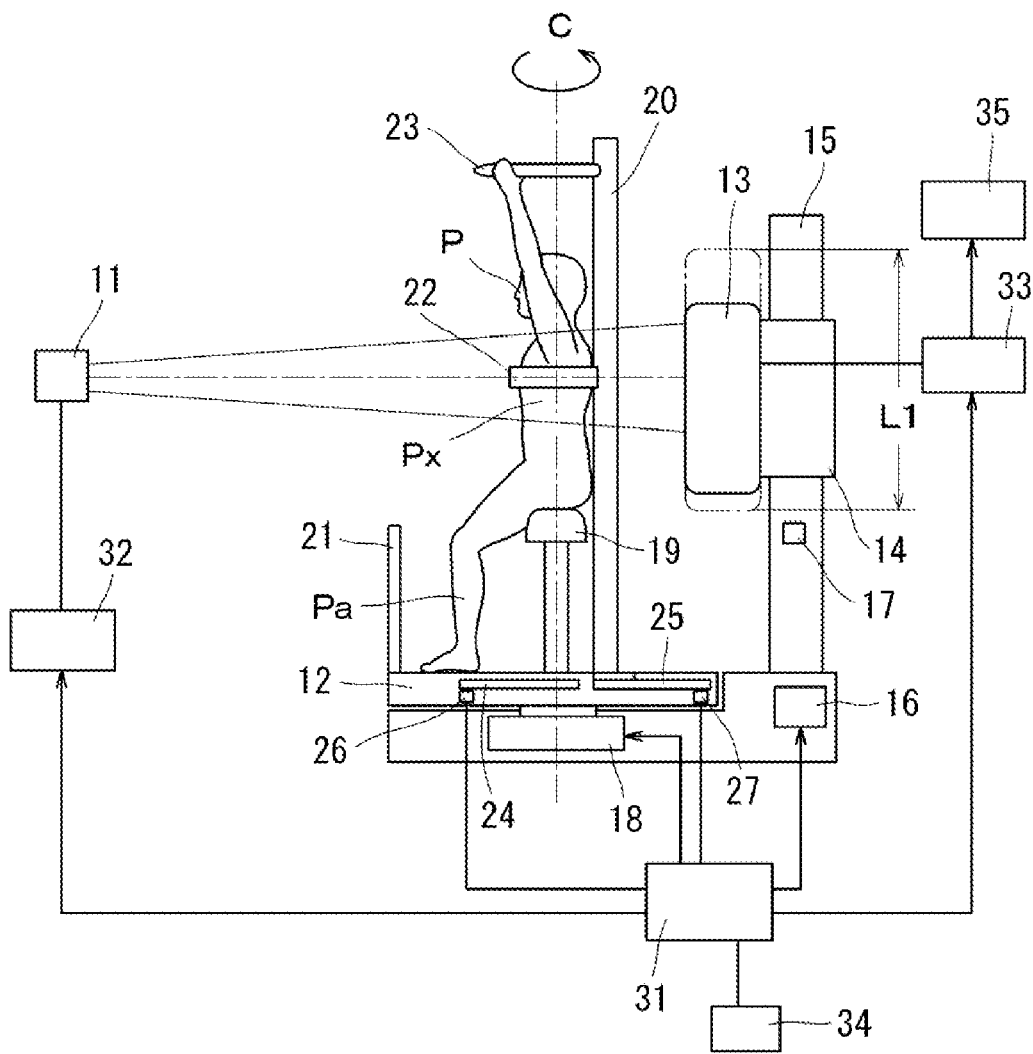

Legend:
11 = X-ray tube
12 = rotating table
13 = X-ray imaging unit
14 = slide unit; 15 = column
16 = up-and-down drawing unit
17 = image taking unit
18 = rotary drive unit
19 = chair; 20 = backrest
21 = lower limb guard
22 = belt; 23 = handle
24 = chair slide member
25 = backrest slide member
26 = chair position detector
27 = backrest position
       detector
31 = control unit
32 = X-ray generation
       apparatus
33 = image taking unit
34 = footswitch
35 = image processing unit Legend:
11 = X-ray tube
12 = rotating table
13 = X-ray imaging unit
14 = slide unit; 15 = column
19 = chair; 20 backrest
21 = lower limb guard
24 = chair slide member
25 = backrest slide member Legend:
11 = X-ray tube
12 = rotating table
13 = X-ray imaging unit
14 = slide unit; 15 = column
16 = up-and-down drawing unit
17 = image taking unit
18 = rotary drive unit
26 = chair position detector
27 = backrest position detector
31 = control unit
32 = X-ray generation apparatus
33 = image taking unit
34 = footswitch
35 = image processing unit Legend:
1 = X-ray tube
2 = rotating table
3 = X-ray imaging unit
4 = lower limb guard

X-RAY IMAGING APPARATUS

BACKGROUND OF THE INVENTION

1. Field of the Invention

The present invention relates to an X-ray imaging apparatus configured to generate an X-ray image of a subject using an X-ray beam passing through the subject.

2. Description of the Related Art

Conventionally, a computed tomography (CT) apparatus for generating a three-dimensional cross-sectional image of a subject is used in the medical area. In order to obtain the three-dimensional cross-sectional image, radiation emitted to the subject from a circumference of the subject is detected and converted into an image signal after it passes through the subject. Then, through reconstruction processing, the image signal is converted into a three-dimensional cross-sectional image.

A helical scanning CT apparatus is a type of apparatus which is commonly used today. The helical scanning CT apparatus is configured such that a radiation source and a radiation detector, configured as a pair, rotate helically around the subject with a virtual body axis of the subject as their axis of rotation to detect intensity of transmitted radiation at a plurality of positions.

On the other hand, in recent years, a CT apparatus has been developed in which a subject, which is positioned between a fixed radiation source and a fixed radiation detector, is rotated in generating a tomographic image. This type of CT apparatus includes a two-dimensional plane sensor as the radiation detector. By emitting a conical radiation beam to the subject, this CT apparatus can generate fluoroscopic images which are necessary in reconstructing a three-dimensional image by a single scan. Further, this CT apparatus eliminates the need for a continuous movement of the subject in the direction of the body axis, which is essential to the common CT apparatus.

An apparatus by which the subject is rotated while its image is taken is discussed in Japanese Patent Application Laid-Open No. 2005-205082. According to this apparatus, it is important to confirm safety of the subject and then rotate the subject after its position is stabilized. A CT apparatus which satisfies such needs is being developed nowadays.

Japanese Patent Application Laid-Open No. 2005-205082 discusses an image taking method in which the subject is rotated while its image is taken. Further, an apparatus discussed in Japanese Patent Application Laid-Open No. 2005-205082 has the capability to secure the safety of the subject and stabilize the posture of the subject during the rotation, which is required during the image taking process.

For example, Japanese Patent Application Laid-Open No. 2006-43193 discusses an apparatus in which a supporting member used for controlling a body motion of the subject is set on a rotating platform. The subject, taking a half-crouching position, is supported by this supporting member on the rotating platform. Further, the CT apparatus discussed in Japanese Patent Application Laid-Open No. 2005-205082 provides a lower limb guard in front of the subject. With this guard, a lower limb of the subject is prevented from contacting a non-rotating portion around the subject during the rotation. By rotating the subject instead of the radiation source and the detector, CT images can be taken with enhanced throughput. Accordingly, CT images are replacing general still images in the area of chest screening.

Further, in order to secure the subject safely, the CT apparatus discussed in Japanese Patent Application Laid-Open No. 2006-43193 detects a state of a member supporting the subject and controls a rotation of a rotation table based on the result of the detection.

However, since radiation detectors of the aforementioned imaging apparatuses are large-sized two-dimensional plane sensors, these imaging apparatuses are generally expensive. Further, from the viewpoint of effective use of a limited installation space in a hospital, a demand for an X-ray imaging apparatus which is capable of taking two different types of images, that is, the CT image and the general still image, is increasing. Japanese Patent Application Laid-Open No. 2005-205082 discusses such an imaging apparatus. When a still image is taken using this imaging apparatus, a space is made on the rotating platform by moving the subject supporting member away from a range of X-ray emission.

In taking a CT image with such an imaging apparatus, the subject is preferably positioned in a close vicinity of an X-ray imaging unit so long as the subject does not contact the unit during the rotation. This contributes to providing a wider reconstruction area, and further, to reducing a possibility of a blurred image. Accordingly, in the actual image taking, it is necessary to set the X-ray imaging unit at a position nearer to the subject compared to the position of the X-ray imaging unit discussed in Japanese Patent Application Laid-Open No. 2005-205082.

In the actual image taking, a lower limb Pa of a subject P seated on a rotating table 2 passes adjacent an X-ray imaging unit 3 while the subject is exposed to the X-ray beam irradiated from an X-ray tube 1 as shown in FIG. 5. Further, if a lower limb guard 4 is provided in front of the subject P, the lower limb guard 4 will rotate under the X-ray imaging unit 3 as well as the lower limb Pa. Thus, in taking a CT image, the X-ray imaging unit 3 needs to be positioned within an imaging range L1.

On the other hand, in taking a still image, as discussed in Japanese Patent Application Laid-Open No. 2005-205082, the subject supporting member is moved away from the imaging area by a moving unit located under the subject supporting member, and the subject is moved closer to the X-ray imaging unit. Then the image is taken while the subject is in full contact with the outer portion of the X-ray imaging unit. On the other hand, the CT apparatus is required to be capable of taking a general still image of a wider range, e.g. the whole body of the subject, from the head to the lower limb. This is because still images are generally taken when patients go through a first medical testing. Therefore, the X-ray imaging unit 3 is required to move up and down in a wider range while a still image is taken compared to when a CT image is taken.

However, if the X-ray imaging unit 3 is configured to cover a wide movable range for the still images, then, the X-ray imaging unit 3 tends to move in a more than necessary range for the CT images. For example, if the X-ray imaging unit is set at a position inappropriately low for the CT imaging, the subject supporting member or the lower limb Pa of the subject P may contact the X-ray imaging unit 3 during rotation. In order to ensure safety, attention needs to be paid when setting the position of the X-ray imaging unit 3. As a result, ease of operability of the X-ray imaging apparatus is reduced.

A similar problem occurs when the image taking mode is changed. If a general still image is taken at a low position by the X-ray imaging unit 3, and then the mode is changed to the CT mode and the subject supporting member is moved, the lower limb Pa of the subject P may contact the X-ray imaging unit 3 if the rotating table 2 is rotated without changing the position of the subject. In this case, safety is reduced as described above.

Furthermore, with respect to a subject-rotating CT imaging apparatus including a plane sensor, a movement of the subject in the body axis direction, which is necessary in the common helical scanning CT apparatus, is not required. On the contrary, images need to be taken from many different angles from a certain height during the CT imaging. Thus, if an imaging apparatus including a height-adjustable X-ray imaging unit moves the X-ray imaging unit up and down during the CT imaging, proper images may not be obtained and therefore reconstruction becomes difficult. Since the conventional apparatus does not include a method for prohibiting the up-and-down movement during the rotation, there is a possibility that the X-ray imaging unit moves up-and-down during the image taking.

SUMMARY OF THE INVENTION

The present invention is directed to an X-ray imaging apparatus which is capable of taking a general still image as well as a CT image, and which is useful in generating an effective image for diagnostics without reducing operability of the vertical position setting of the X-ray imaging unit and, further, without reducing safety.

According to an aspect of the present invention, an X-ray imaging apparatus includes an X-ray imaging unit, a rotation unit configured to rotate a subject about an axis of rotation relative to the X-ray imaging unit, a support configured to support the subject, and a limiter configured to limit a range in which the X-ray imaging unit is moveable along the axis of rotation in dependence upon the position of the support relative to the axis of rotation.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 1 illustrates a configuration of an X-ray imaging apparatus in a CT imaging mode according to an exemplary embodiment of the present invention.

DETAILED DESCRIPTION OF THE EMBODIMENTS

Figure 2:
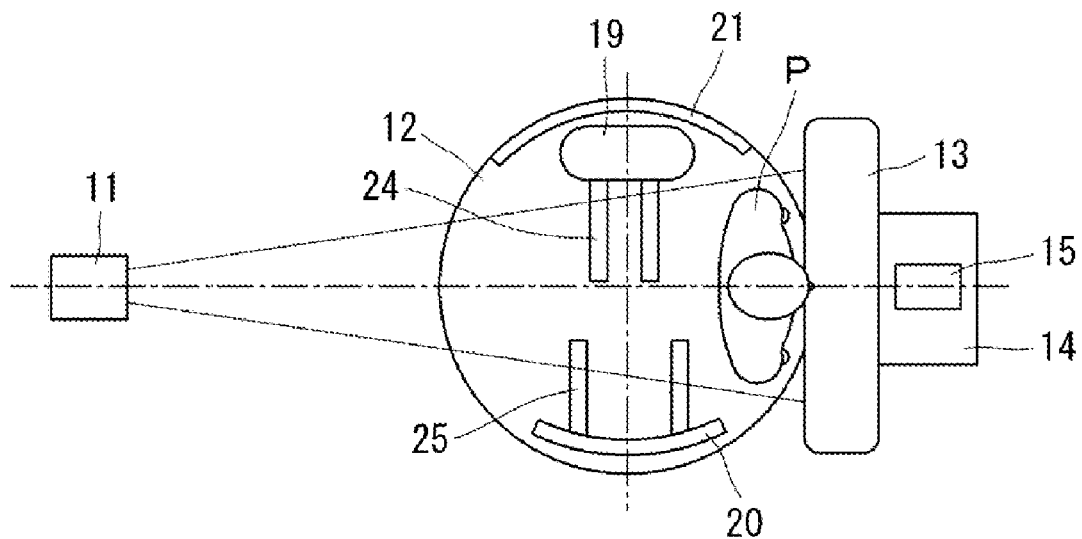
FIG. 2 is a top view of a configuration of the X-ray imaging apparatus in a still-image taking mode according to an exemplary embodiment of the present invention.

Various exemplary embodiments, features, and aspects of the invention will now be described in detail with reference to the drawings.

FIG. 1 illustrates a configuration of an X-ray imaging apparatus in a CT imaging mode in which the subject (P) is rotated during image taking according to an exemplary embodiment of the present invention. In front of an X-ray tube 11, an X-ray imaging unit 13 which is, for example, a plane sensor, is arranged facing the X-ray tube 11. A subject P on a rotating table 12 is positioned between the X-ray tube 11 and the X-ray imaging unit 13. The rotating table 12 is rotatable 360 degrees. The X-ray imaging unit 13 is moveably attached to a column 15 through a slide unit 14. The slide unit 14 is driven up-and-down by an up-and-down drive unit 16. The lowest position of the X-ray imaging unit 13 can be detected by an image taking unit position detector 17.

The rotating table 12 is supported by a rotary drive unit 18. A chair 19 on which the subject P sits, a backrest 20 against which the subject P presses its back, and a lower limb guard 21 used for protecting the lower limb Pa of the subject P from the X-ray are located on the rotating table 12.

The chair 19 is set in the vicinity of an axis of rotation C of the rotating table 12. The subject P presses its back against the backrest 20 while it is seated on the chair 19. The backrest 20 is long in the vertical direction and its cross section is arched so that the subject P can easily press its back against it. A belt 22 and a handle 23 for securing the subject P are provided coupled to the backrest 20. A position of the backseat 20 in the horizontal direction is set so that a virtual body axis of the subject P is substantially coaxial with the axis of rotation C of the rotating table 12 when subject P is pressed against the backrest 20.

The lower limb guard 21 is arched so that it matches the circular shape of the rotating table 12. The lower limb guard 21 is provided to protect the lower limb Pa of the subject P from contacting a non-rotating portion surrounding the rotating table 12 during rotation.

The chair 19 and the backrest 20 which constitute the subject supporting member can be removed from a position of CT imaging to a position outside the image taking range by a chair slide member 24 and a backrest slide member 25. Thus, the still-image taking is not interrupted by the subject supporting member. Positions of the chair 19 and the backrest 20 are detected by a chair position detector 26 and a backrest position detector 27.

A control unit 31 which controls the X-ray imaging apparatus is connected to an X-ray generation apparatus 32 which generates the X-ray beam irradiated from the X-ray tube 11, the up-and-down drive unit 16, a rotary drive unit 18, and an image taking unit 33 which captures an image taken by the X-ray imaging unit 13. Further, the control unit 31 is connected to the image taking unit position detector 17, the chair position detector 26, the backrest position detector 27, and a footswitch 34. The output of the image taking unit 33 is input to an image processing unit 35.

The slide unit 14 moves the X-ray imaging unit 13 up-and-down in the vertical direction along the column 15 driven by the up-and-down drive unit 16. The drive control by the up-and-down drive unit 16 is performed based on an instruction of the control unit 31 according to, for example, the operation of a footswitch 34 by an operator. Further, whether the vertical position of the X-ray imaging unit 13 is within the CT imaging range L1 of the CT imaging, is detected by the image taking unit position detector 17. The result of the detection is sent to the control unit 31. The lowest position of the CT imaging range L1 is set to a predetermined height so that the lower limb guard 21 of the subject supporting member does not enter the image taking area and that the lower limb Pa of the subject P does not contact the X-ray imaging unit 13.

Whether the CT image or the still image is to be taken is detected by the chair position detector 26 and the backrest position detector 27, which are supporting member position detection units. The result of the detection is sent to the control unit 31.

In taking a CT image, the control unit 31 drives the rotary drive unit 18 according to an imaging request signal and controls the rotation of the rotating table 12. When the rotating table 12 reaches a predetermined rotation state, the X-ray irradiation from the X-ray tube 11 of the CT imaging is started. In this state, even if the footswitch 34 is operated, the control unit 31 does not move the X-ray imaging unit 13 up or down and keeps the X-ray imaging unit 13 in that position. In this way, images of a position taken from many directions can be obtained.

In synchronization with this irradiation, the control unit 31 controls the image taking unit 33 so that the X-ray that passed through the subject P is captured by the X-ray imaging unit 13 as image data. The image processing unit 35 processes the image data taken from all directions around the subject and reconstructs a three-dimensional tomographic image.

The control unit 31 may be set so that the X-ray imaging unit 13 is not moved up-and-down while the rotating table 12 is rotating, regardless of whether the X-ray beam is emitted.

Figure 3:
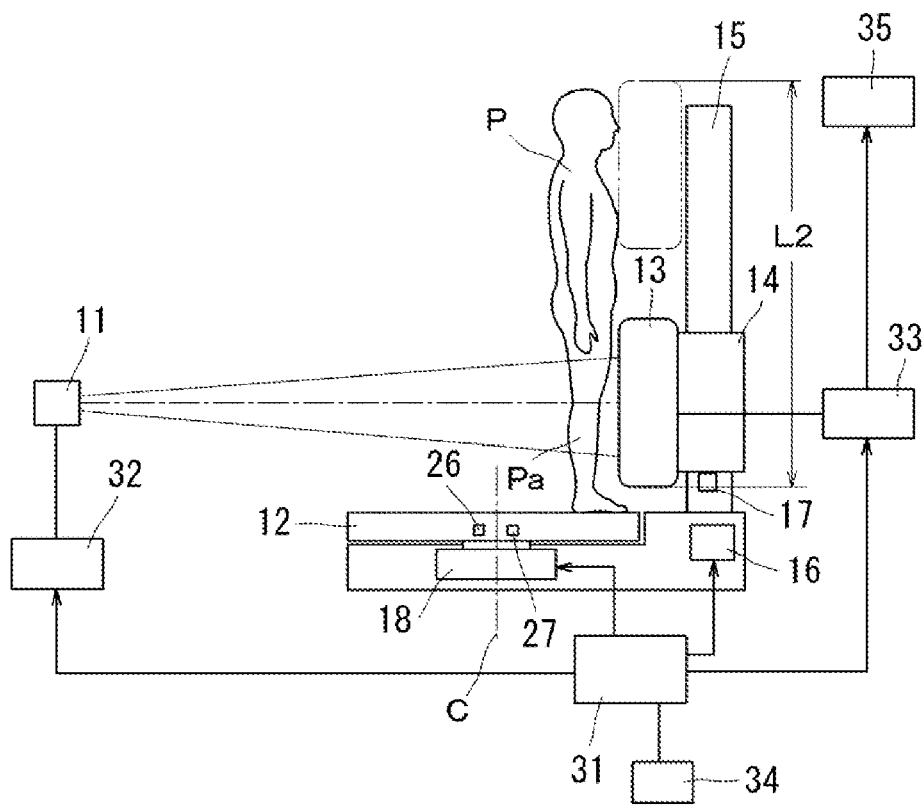
FIG. 3 is a side view of the configuration of the X-ray imaging apparatus in the still-image taking mode according to an exemplary embodiment of the present invention.

FIG. 2 is a top view of the configuration of the X-ray imaging apparatus in the still-image taking mode. The rotating table 12 is rotated 90 degrees clockwise from the state shown in FIG. 1 and the positions of the chair 19 and the backrest 20 are changed from the positions during the CT imaging. FIG. 3 is a side view of the configuration of the X-ray imaging apparatus in the state illustrated in FIG. 2. Since the chair 19 and the backrest 20 are moved on the rotating table 12 in a circumference direction by the chair slide member 24 and the backrest slide member 25 respectively, the body of the subject P can fully contact the X-ray imaging unit 13 whilst taking the image.

The X-ray beam emitted from the X-ray tube 11 passes between the chair 19 and the backrest 20 and is irradiated onto the subject P. In this case, an image of an arbitrary portion Px of the whole body, from the head of the subject P to its lower limb Pa, can be taken since the irradiation is not disturbed. The image is taken depending on the position of the imaging range L2 of the X-ray imaging unit 13.

In taking a still image of the lower limb Pa of the subject P, the X-ray imaging unit 13 may be set at a low position. Even if the chair 19 and the backrest 20 are changed to the CT imaging mode after the taking of the still image is finished, the X-ray imaging unit 13 remains at the position for the still image. If the rotating table 12 is rotated in this state, the lower limb Pa, for example, may hit the X-ray imaging unit 13. According to the present exemplary embodiment, however, such a possibility is eliminated.

The change of the positions of the chair 19 and the backrest 20 to the positions for the CT imaging is detected by the chair position detector 26 and the backrest position detector 27. Signals that the positions of the chair 19 and the backrest 20 are changed are sent to the control unit 31. Even when the control unit 31 receives such a signal, the image taking unit position detector 17 detects and sends a signal indicating that the X-ray imaging unit 13 is not at the CT imaging position. In this state, the control unit 31 controls the rotating table 12 so that it does not rotate even if an instruction to move the rotating table 12 is given by the operator. At the same time, a sign indicating that the X-ray imaging unit 13 needs to be moved is displayed on a display unit (not shown).

In this state, the control unit 31 allows only the upward movement of the X-ray imaging unit. When the operator moves the X-ray imaging unit upwards using the footswitch 34 and the X-ray imaging unit 13 moves within the CT imaging range L1 for the CT imaging, the sign on the display unit disappears. Alternatively, the X-ray imaging unit 13 may be controlled so that the X-ray imaging unit 13 moves automatically up to the lowest position of the CT imaging range L1 when the sign is displayed. In this way, the problem that occurs when changing the still-image taking mode to the CT imaging mode can be prevented.

Figure 4:
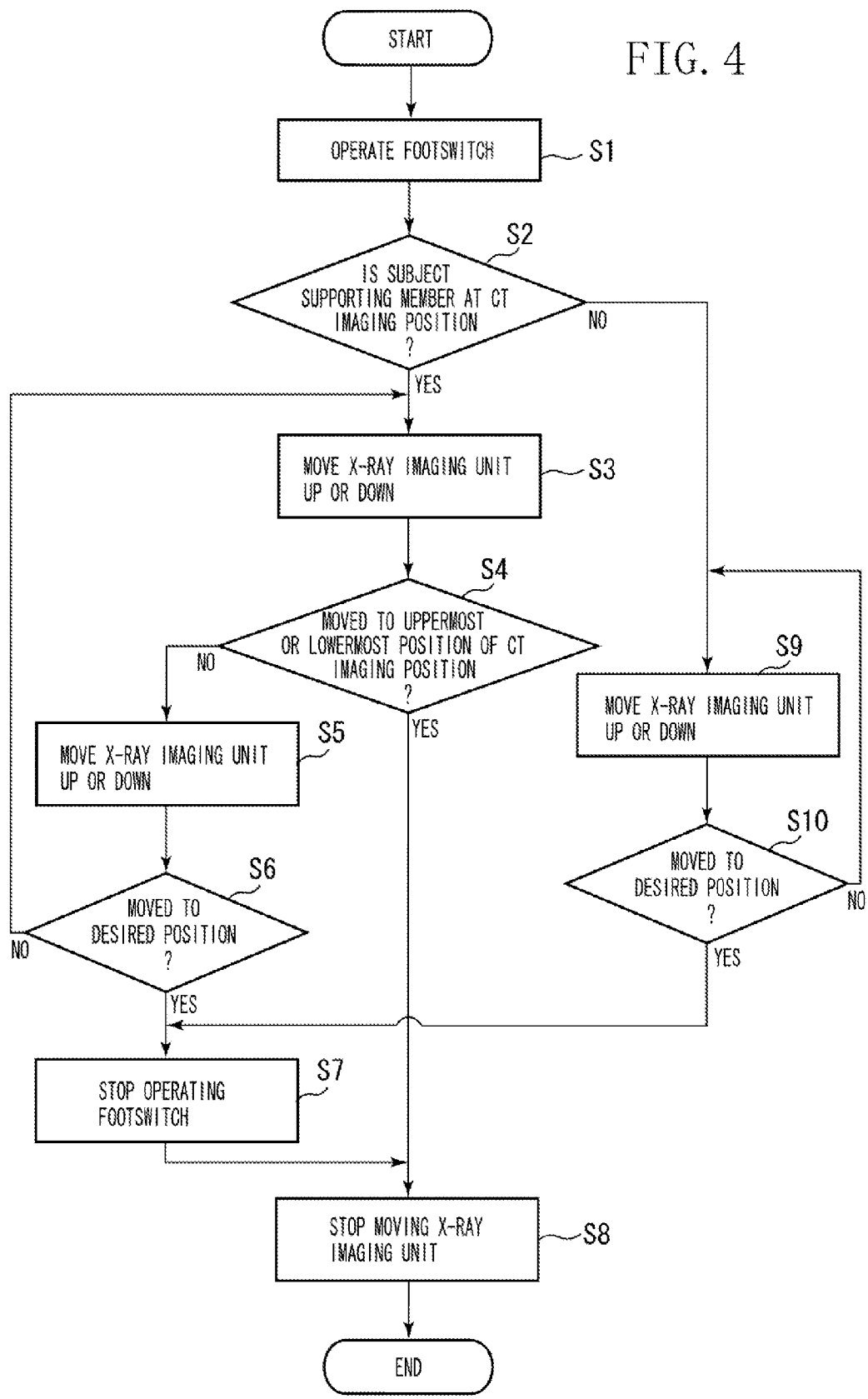
FIG. 4 is a flowchart illustrating an up-and-down movement of the X-ray imaging unit of the X-ray imaging apparatus according to an exemplary embodiment of the present invention.
Figure 5:
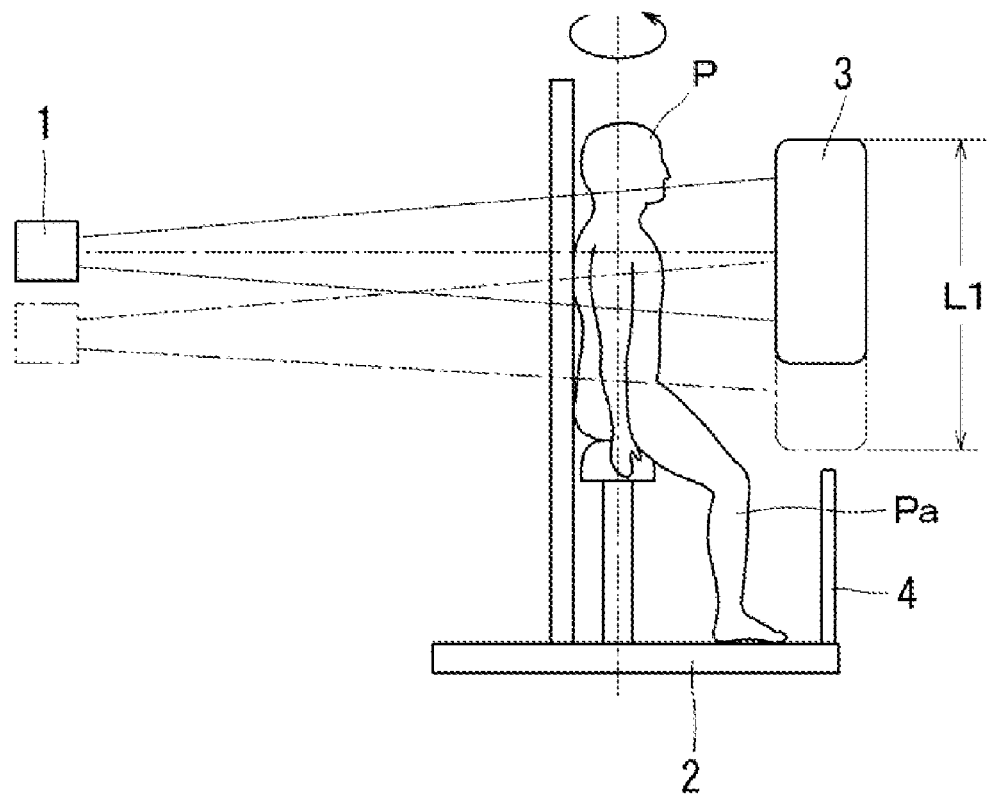
FIG. 5 illustrates a configuration of a conventional X-ray imaging apparatus.

FIG. 4 is a flowchart illustrating the adjustment of the up-and-down position of the X-ray imaging unit 13. In step S1, in order to adjust a position of the X-ray imaging unit 13, the operator operates the footswitch 34. In step S2, the control unit 31 determines whether the subject supporting members of the chair 19 and the backrest 20, are in the CT imaging position based on a signal from the chair position detector 26 and the backrest position detector 27.

If the CT imaging apparatus is in the CT imaging position as illustrated in FIG. 1 (YES in step S2), then according to steps S3 to S6, the control unit 31 permits the up-and-down movement of the X-ray imaging unit 13 based on an operation of the footswitch 34 so long as a signal from the image taking unit position detector 17 indicates that the X-ray imaging unit 13 is in the CT imaging range L1. In step S7, the operator removes his foot from the footswitch 34 when the X-ray imaging unit 13 reaches a desired position and stops the up-and-down movement in step S8.

However, if the control unit 31 determines that the X-ray imaging unit 13 has reached the uppermost or lowermost position of the CT imaging range (YES in step S4), then in step S8, the control unit 31 controls the X-ray imaging unit 13 to stop at that position and that further up-and-down movement is not made. In this way, the X-ray imaging unit 13 will be always set in the CT imaging range L1 during the CT imaging mode.

Further, if the subject supporting member is in a still-image taking mode as shown in FIGS. 2 and 3 (NO in step S2), then in steps S9 and S10, the control unit 31 controls the X-ray imaging unit 13 so that the up-and-down movement of the X-ray imaging unit 13 is performed according to an input from the footswitch 34 regardless of the signal from the image taking unit position detector 17. In this way, the X-ray imaging unit 13 is able to move within a wide still image imaging range L2 (larger than L1) which is shown in FIG. 3 during the still-image taking. Accordingly, an image of the whole body of the subject P, from head to the lower limb Pa, can be taken.

According to the X-ray imaging apparatus of the exemplary embodiment of the present invention, general still images as well as CT images can be taken. In addition, effective images for diagnostics can be obtained without reducing safety and operability in setting a vertical position of the X-ray imaging unit.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2007-127539 filed May 14, 2007, which is hereby incorporated by reference herein in its entirety.

What is claimed is:

1. An X-ray imaging apparatus comprising:
   an X-ray imaging unit;
   a rotating driving unit configured to control a rotation of a table rotating on an axis of rotation;

a control unit configured to control the rotating driving unit;

a support configured to support a subject, which changes a position on the table between still-image taking and computed tomography (CT) imaging;

a lower limb guard configured to guard a lower limb of the subject on the table;

an image taking unit position detector configured to detect a position of the X-ray imaging unit; and a limiter configured to limit a range in which the X-ray imaging unit is moveable along the axis of rotation in dependence upon the position of the support relative to the axis of rotation, wherein the limiter limits a position of the X-ray imaging unit within the range in which an image of the lower limb guard is not taken when the support is at the CT imaging position, and wherein the control unit keeps rotation of the rotating unit in a suspended state when the support is at the CT imaging position and the position of the X-ray imaging unit is not within the range.

2. The X-ray imaging apparatus according to claim 1, further comprising a detector configured to detect whether the support is at the CT imaging position, wherein the limiter is configured to limit the range in which the X-ray imaging unit is moved based on an output of the detector.

3. The X-ray imaging apparatus according to claim 1, wherein the rotating driving unit is configured to allow the rotating table to rotate when the range in which the X-ray imaging unit is moved along the axis of rotation is limited.

4. The X-ray imaging apparatus according to claim 3, wherein the control unit is further configured to inhibit the movement of the X-ray imaging unit when the rotating table is rotating.

* * * * *